United States Patent
Yuen et al.

(10) Patent No.: US 7,462,744 B1
(45) Date of Patent: Dec. 9, 2008

(54) SYNTHESIS OF AMINES USING BORON-CONTAINING MOLECULAR SIEVE CHA

(75) Inventors: Lun-Teh Yuen, Orinda, CA (US); Stacey I. Zones, San Francisco, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 11/941,715

(22) Filed: Nov. 16, 2007

Related U.S. Application Data

(63) Continuation-in-part of application No. 11/266,083, filed on Nov. 2, 2005, now abandoned.

(60) Provisional application No. 60/632,006, filed on Nov. 30, 2004.

(51) Int. Cl.
*C07C 209/16* (2006.01)
(52) U.S. Cl. ...................... 564/479; 564/474
(58) Field of Classification Search .............. None
See application file for complete search history.

(56) References Cited

U.S. PATENT DOCUMENTS

| | | | |
|---|---|---|---|
| 2,942,932 A | 6/1960 | Elliott | |
| 3,030,181 A | 4/1962 | Milton | |
| 3,699,683 A | 10/1972 | Tourtellotte et al. | |
| 3,767,453 A | 10/1973 | Hoekstra | |
| 3,785,993 A | 1/1974 | Hoekstra | |
| 3,920,583 A | 11/1975 | Pugh | |
| 4,297,323 A | 10/1981 | Ritscher et al. | |
| 4,297,328 A | 10/1981 | Ritscher et al. | |
| 4,496,786 A | 1/1985 | Santilli et al. | |
| 4,528,279 A | 7/1985 | Suzuki et al. | |
| 4,677,242 A | 6/1987 | Kaiser | |
| 4,737,592 A | 4/1988 | Abrams et al. | |
| 4,760,044 A | 7/1988 | Joy, III et al. | |
| 4,791,091 A | 12/1988 | Bricker et al. | |
| 4,861,938 A | 8/1989 | Lewis et al. | |
| 4,868,148 A | 9/1989 | Henk et al. | |
| 4,868,149 A | 9/1989 | Bricker | |
| 5,078,979 A | 1/1992 | Dunne | |
| 6,508,860 B1 | 1/2003 | Kulkarni et al. | |
| 6,709,644 B2 | 3/2004 | Zones et al. | |
| 2003/0069449 A1 | 4/2003 | Zones et al. | |
| 2003/0089227 A1 | 5/2003 | Hasse et al. | |
| 2003/0176751 A1 | 9/2003 | Strohmaier et al. | |

FOREIGN PATENT DOCUMENTS

| | | |
|---|---|---|
| CA | 1 205 980 | 6/1986 |
| GB | 868846 | 5/1961 |

OTHER PUBLICATIONS

Donald W. Breck, Zeolite Molecular Sieves, Jul. 1972, 73-11028, John Wiley & Sons, Inc. Canada.
R. M. Barrer and J. W. Baynham, The Hydrothermal Chemistry of the Silicates, Synthetic Potassium Aluminosilicates, 1955, 2882-2891, Imperial College of Science, London S.W.7.
W. M. Meier and D. H. Olson, Atlas of Zeolite Structure Types, 1978, 25, Structure Commission on the International Zeolite Association.
Abstract to Russian Article and Copy of Russian Article Kollist A; Paris J., Isolation Characteristics, and Use of Polysac Charides From Agar-Containing Algae, 1980, 66065.
M. A. Camblor, et al., Synthesis of All-Silica and High-Silica Molecular Sieves in Fluoride Media, Topics in Catalysis 9, 1999, 59-76, J. C. Baltzer AG, Science Publishers.
Christopher W. Jones, Synthesis of Hydrophobic Molecular Sieves by Hydrothermal Treatment with Acetic Acid, Chem. Matter, 2001, 13, 1041-1050, Published on Web Jan. 23, 2001.

*Primary Examiner*—Brian J Davis
(74) *Attorney, Agent, or Firm*—Richard J. Sheridan; Susan Abernathy

(57) ABSTRACT

A process for producing methylamine or dimethylamine comprising reacting methanol, dimethyl ether or a mixture thereof, and ammonia in the gaseous phase in the presence of a catalyst comprising a boron-containing molecular sieve having the CHA crystal structure; and comprising (1) silicon oxide and (2) boron oxide or a combination of boron oxide and aluminum oxide, iron oxide, titanium oxide, gallium oxide and mixtures thereof; and wherein the mole ratio of silicon oxide to boron oxide in said boron-containing molecular sieve is between 15 and 125. Also a method for producing methylamine or dimethylamine comprising selecting the boron-containing molecular sieve having the CHA crystal structure and the desired mole ratio of silicon oxide to boron oxide and reacting methanol, diemethyl ether or a mixture thereof and ammonia in the presence of the catalyst.

14 Claims, No Drawings

SYNTHESIS OF AMINES USING BORON-CONTAINING MOLECULAR SIEVE CHA

This application claims benefit under 35 USC 119 of Provisional Application 60/632,006, filed Nov. 30, 2004 and is a Continuation-in-Part of Non Provisional Application 11/266,083 filed Nov. 2, 2005 now abandoned.

BACKGROUND

Chabazite, which has the crystal structure designated "CHA", is a natural zeolite with the approximate formula $Ca_6Al_{12}Si_{24}O_{72}$. Synthetic forms of chabazite are described in "Zeolite Molecular Sieves" by D. W. Breck, published in 1973 by John Wiley & Sons. The synthetic forms reported by Breck are: zeolite "K-G", described in J. Chem. Soc., p. 2822 (1956), Barrer et al.; zeolite D, described in British Patent No. 868,846 (1961); and zeolite R, described in U.S. Pat. No. 3,030,181, issued Apr. 17, 1962 to Milton et al. Chabazite is also discussed in "Atlas of Zeolite Structure Types" (1978) by W. H. Meier and D. H. Olson.

The K-G zeolite material reported in the J. Chem. Soc. Article by Barrer et al. is a potassium form having a silica:alumina mole ratio (referred to herein as "SAR") of 2.3:1 to 4.15:1. Zeolite D reported in British Patent No. 868,846 is a sodium-potassium form having a SAR of 4.5:1 to 4.9:1. Zeolite R reported in U.S. Pat. No. 3,030,181 is a sodium form which has a SAR of 3.45:1 to 3.65:1.

Citation No. 93:66052y in Volume 93 (1980) of Chemical Abstracts concerns a Russian language article by Tsitsishrili et al. in *Soobsch. Akad. Nauk. Gruz.* SSR 1980, 97(3) 621-4. This article teaches that the presence of tetramethylammonium ions in a reaction mixture containing $K_2O$—$Na_2O$—$SiO_2$—$Al_2O_3$—$H_2O$ promotes the crystallization of chabazite. The zeolite obtained by the crystallization procedure has a SAR of 4.23.

The molecular sieve designated SSZ-13, which has the CHA crystal structure, is disclosed in U.S. Pat. No. 4,544,538, issued Oct. 1, 1985 to Zones. SSR-13 is prepared from nitrogen-containing cations derived from 1-adamantamine, 3-quinuclidinol and 2-exo-aminonorbornane. Zones discloses that the SSZ-13 of U.S. Pat. No. 4,544,538 has a composition, as-synthesized and in the anhydrous state, in terms of mole ratios of oxides as follows:

(0.5 to 1.4)$R_2O$:(0 to 0.5)$M_2O$:$W_2O_3$:(greater than 5)$YO_2$ wherein M is an alkali metal cation, W is selected from aluminum, gallium and mixtures thereof, Y is selected from silicon, germanium and mixtures thereof, and R is an organic cation. U.S. Pat. No. 4,544,538 does not, however, disclose boron-containing SSZ-13.

U.S. Pat. No. 6,709,644, issued Mar. 23, 2004 to Zones et al., discloses zeolites having the CHA crystal structure and having small crystalline sizes. It does not, however, disclose a CHA zeolite containing boron. It is disclosed that the zeolite can be used for separation of gasses (e.g., separating carbon dioxide from natural gas), and in catalysts used for the reduction of oxides of nitrogen in a gas stream (e.g., automotive exhaust), converting lower alcohols and other oxygenated hydrocarbons to liquid products, and for producing dimethylamine.

U.S. Patent Publication US 2003/0176751A1 discloses zeolites having the CHA crystal structure with a silica/alumina molar ratio below and above 265. The reaction mixture with hydrofluoric acid used to produce the zeolite has a low Wt % yield of zeolite based on silica. It also does not produce zeolites having the CHA crystal structure wherein the mole ratio of silicon oxide to boron oxide in the zeolite is between 15 and 125.

SUMMARY OF THE INVENTION

There is provided a process for producing methylamine or dimethylamine comprising reacting methanol, dimethyl ether or a mixture thereof and ammonia in the gaseous phase in the presence of a catalyst comprising a boron-containing molecular sieve having the CHA crystal structure and comprising (1) silicon oxide and (2) boron oxide or a combination of boron oxide and aluminum oxide, iron oxide, titanium oxide, gallium oxide and mixtures thereof; and wherein the mole ratio of silicon oxide to boron oxide in said boron-containing molecular sieve is between 15 and 125.

There is also provided a method for producing methylamine or dimethylamine, comprising:
a. selecting a catalyst comprising a boron-containing molecular sieve having a CHA crystal structure and a mole ratio of silicon oxide to boron oxide between 15 and 125; and
b. reacting methanol, dimethyl ether or a mixture thereof, and ammonia in the presence of the catalyst.

DETAILED DESCRIPTION

The present invention relates to molecular sieves having the CHA crystal structure and containing boron in their crystal framework.

Boron-containing CHA molecular sieves can be suitably prepared from an aqueous reaction mixture containing sources of sources of an oxide of silicon; sources of boron oxide or a combination of boron oxide and aluminum oxide, iron oxide, titanium oxide, gallium oxide and mixtures thereof; optionally sources of an alkali metal or alkaline earth metal oxide; and a cation derived from 1-adamantamine; 3-quinuclidinol or 2-exo-aminonorbornane. The mixture should have a composition in terms of mole ratios falling within the ranges shown in Table A below:

TABLE A

| | |
|---|---|
| $YO_2/W_aO_b$ | >2-2,000 |
| $OH^-/YO_2$ | 0.2-0.45 |
| $Q/YO_2$ | 0.2-0.45 |
| $M_{2/n}O/YO_2$ | 0-0.25 |
| $H_2O/YO_2$ | 22-80 | wherein Y is silicon; W is boron or a combination of boron and aluminum, iron, titanium, gallium and mixtures thereof; M is an alkali metal or alkaline earth metal; n is the valence of M (i.e., 1 or 2) and Q is a quaternary ammonium cation derived from 1-adamantamine, 3-quinuclidinol or 2-exo-aminonorbornane (commonly known as a structure directing agent or "SDA").

The quaternary ammonium cation derived from 1-adamantamine can be a N,N,N-trialkyl-1-adamantammonium cation which has the formula:

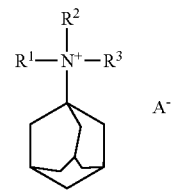

where $R^1$, $R^2$, and $R^3$ are each independently a lower alkyl, for example methyl. The cation is associated with an anion, $A^-$, which is not detrimental to the formation of the molecular sieve. Representation of such anions include halogens, such as fluoride, chloride, bromide and iodide; hydroxide; acetate;

sulfate and carboxylate. Hydroxide is the preferred anion. It may be beneficial to ion exchange, for example, a halide for hydroxide ion, thereby reducing or eliminating the alkali metal or alkaline metal hydroxide required.

The quaternary ammonium cation derived from 3-quinuclidinol can have the formula:

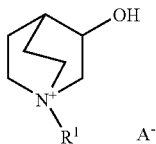

where $R^1$ is defined as above.

The quaternary ammonium cation derived from 2-exo-aminonorbornane can have the formula:

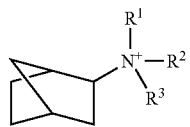

where $R^1$, $R^2$, $R^3$ and A are as defined above.

The reaction mixture is prepared using standard molecular sieve preparation techniques. Typical sources of silicon oxide include fumed silica, silicates, silica hydrogel, silicic acid, colloidal silica, tetra-alkyl orthosilicates, and silica hydroxides. Sources of boron oxide include borosilicate glasses and other reactive boron compounds. These include borates, boric acid and borate esters. Typical sources of aluminum oxide include aluminates, alumina, hydrated aluminum hydroxides, and aluminum compounds such as $AlCl_3$ and $Al_2(SO_4)_3$. Sources of other oxides are analogous to those for silicon oxide, boron oxide and aluminum oxide.

It has been found that seeding the reaction mixture with CHA crystals both directs and accelerates the crystallization, as well as minimizing the formation of undesired contaminants. In order to produce pure phase boron-containing CHA crystals, seeding may be required. When seeds are used, they can be used in an amount that is about 2-3 weight percent based on the weight of $YO_2$.

The reaction mixture is maintained at an elevated temperature until CHA crystals are formed. The temperatures during the hydrothermal crystallization step are typically maintained from about 120° C. to about 160° C. It has been found that a temperature below 160° C., e.g., about 120° C. to about 140° C., is useful for producing boron-containing CHA crystals without the formation of secondary crystal phases.

The crystallization period is typically greater than 1 day and preferably from about 3 days to about 7 days. The hydrothermal crystallization is conducted under pressure and usually in an autoclave so that the reaction mixture is subject to autogenous pressure. The reaction mixture can be stirred, such as by rotating the reaction vessel, during crystallization.

Once the boron-containing CHA crystals have formed, the solid product is separated from the reaction mixture by standard mechanical separation techniques such as filtration. The crystals are water-washed and then dried, e.g., at 90° C. to 150° C. for from 8 to 24 hours, to obtain the as-synthesized crystals. The drying step can be performed at atmospheric or subatmospheric pressures.

The boron-containing CHA molecular sieve has a composition, as-synthesized and in the anhydrous state, in terms of mole ratios of oxides as indicated in Table B below:

As-Synthesized Boron-Containing CHA Composition

TABLE B

| | |
|---|---|
| $YO_2/W_cO_d$ | 20-2,000 |
| $M_{2/n}O/YO_2$ | 0-0.03 |
| $Q/YO_2$ | 0.02-0.05 | where Y, W, M, n and Q are as defined above.

The boron-containing CHA molecular sieves, as-synthesized, have a crystalline structure whose X-ray powder diffraction ("XRD") pattern shows the following characteristic lines:

TABLE I

As-Synthesized Boron-Containing CHA XRD

| 2 Theta[a] | d-spacing (Angstroms) | Relative Intensity[b] |
|---|---|---|
| 9.68 | 9.13 | S |
| 14.17 | 6.25 | M |
| 16.41 | 5.40 | VS |
| 17.94 | 4.94 | M |
| 21.13 | 4.20 | VS |
| 25.21 | 3.53 | VS |
| 26.61 | 3.35 | W-M |
| 31.11 | 2.87 | M |
| 31.42 | 2.84 | M |
| 31.59 | 2.83 | M |

[a] ±0.10
[b] The X-ray patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

Table IA below shows the X-ray powder diffraction lines for as-synthesized boron-containing CHA including actual relative intensities.

TABLE IA

As-Synthesized Boron-Containing CHA XRD

| 2 Theta[a] | d-spacing (Angstroms) | Relative Intensity (%) |
|---|---|---|
| 9.68 | 9.13 | 55.2 |
| 13.21 | 6.70 | 5.4 |
| 14.17 | 6.25 | 33.5 |
| 16.41 | 5.40 | 81.3 |
| 17.94 | 4.94 | 32.6 |
| 19.43 | 4.56 | 6.8 |
| 21.13 | 4.20 | 100 |
| 22.35 | 3.97 | 15.8 |
| 23.00 | 3.86 | 10.1 |
| 23.57 | 3.77 | 5.1 |
| 25.21 | 3.53 | 78.4 |
| 26.61 | 3.35 | 20.2 |
| 28.37 | 3.14 | 6.0 |
| 28.57 | 3.12 | 4.4 |
| 30.27 | 2.95 | 3.9 |
| 31.11 | 2.87 | 29.8 |
| 31.42 | 2.84 | 38.3 |
| 31.59 | 2.83 | 26.5 |
| 32.27 | 2.77 | 1.4 |
| 9.68 | 9.13 | 55.2 |
| 13.21 | 6.70 | 5.4 |
| 14.17 | 6.25 | 33.5 |
| 16.41 | 5.40 | 81.3 |
| 17.94 | 4.94 | 32.6 |
| 19.43 | 4.56 | 6.8 |
| 21.13 | 4.20 | 100 |
| 22.35 | 3.97 | 15.8 |
| 23.00 | 3.86 | 10.1 |

TABLE IA-continued

As-Synthesized Boron-Containing CHA XRD

| 2 Theta[a] | d-spacing (Angstroms) | Relative Intensity (%) |
|---|---|---|
| 23.57 | 3.77 | 5.1 |
| 25.21 | 3.53 | 78.4 |
| 26.61 | 3.35 | 20.2 |
| 28.37 | 3.14 | 6.0 |
| 28.57 | 3.12 | 4.4 |
| 30.27 | 2.95 | 3.9 |
| 31.11 | 2.87 | 29.8 |
| 31.42 | 2.84 | 38.3 |
| 31.59 | 2.83 | 26.5 |
| 32.27 | 2.77 | 1.4 |
| 33.15 | 2.70 | 3.0 |
| 33.93 | 2.64 | 4.7 |
| 35.44 | 2.53 | 3.9 |
| 35.84 | 2.50 | 1.2 |
| 36.54 | 2.46 | 10.9 |
| 39.40 | 2.29 | 1.8 |
| 40.02 | 2.25 | 1.3 |
| 40.44 | 2.23 | 1.0 |
| 40.73 | 2.21 | 6.0 |

[a] ±0.10

After calcination, the boron-containing CHA molecular sieves have a crystalline structure whose X-ray powder diffraction pattern include the characteristic lines shown in Table II:

TABLE II

Calcined Boron-Containing CHA XRD

| 2 Theta[a] | d-spacing (Angstroms) | Relative Intensity |
|---|---|---|
| 9.74 | 9.07 | VS |
| 13.12 | 6.74 | M |
| 14.47 | 6.12 | W |
| 16.38 | 5.41 | W |
| 18.85 | 4.78 | M |
| 21.07 | 4.21 | M |
| 25.98 | 3.43 | W |
| 26.46 | 3.37 | W |
| 31.30 | 2.86 | W |
| 32.15 | 2.78 | W |

[a] ±0.10

Table IIA below shows the X-ray powder diffraction lines for calcined boron-containing CHA including actual relative intensities.

TABLE IIA

Calcined Boron-Containing CHA XRD

| 2 Theta[a] | d-spacing (Angstroms) | Relative Intensity (%) |
|---|---|---|
| 9.74 | 9.07 | 100 |
| 13.12 | 6.74 | 29.5 |
| 14.47 | 6.12 | 4.6 |
| 16.38 | 5.41 | 14.2 |
| 18.85 | 4.78 | 22.1 |
| 19.60 | 4.53 | 2.2 |
| 21.07 | 4.21 | 32.9 |
| 22.84 | 3.89 | 2.2 |
| 23.68 | 3.75 | 0.8 |
| 25.98 | 3.43 | 13.1 |
| 26.46 | 3.37 | 8.7 |
| 28.27 | 3.15 | 1.3 |
| 29.24 | 3.05 | 1.6 |
| 30.32 | 2.95 | 1.7 |
| 31.30 | 2.86 | 14.4 |
| 32.15 | 2.78 | 9.0 |
| 32.56 | 2.75 | 0.2 |
| 35.26 | 2.54 | 2.4 |

[a] ±0.15

The X-ray powder diffraction patterns were determined by standard techniques. The radiation was the K-alpha/doublet of copper and a scintillation counter spectrometer with a strip-chart pen recorder was used. The peak heights I and the positions, as a function of 2 Theta where Theta is the Bragg angle, were read from the spectrometer chart. From these measured values, the relative intensities, 100×I/Io, where Io is the intensity of the strongest line or peak, and d, the interplanar spacing in Angstroms corresponding to the recorded lines, can be calculated.

Variations in the diffraction pattern can result from variations in the mole ratio of oxides from sample to sample. The molecular sieve produced by exchanging the metal or other cations present in the molecular sieve with various other cations yields a similar diffraction pattern, although there can be shifts in interplanar spacing as well as variations in relative intensity. Calcination can also cause shifts in the X-ray diffraction pattern. Also, the symmetry can changed based on the relative amounts of boron and aluminum in the crystal structure. Notwithstanding these perturbations, the basic crystal lattice structure remains unchanged.

The molecular sieve of the present invention can be used in a catalyst to prepare methylamine or dimethylamine. Dimethylamine is generally prepared in industrial quantities by continuous reaction of methanol (and/or dimethylether) and ammonia in the presence of a silica-alumina catalyst. The reactants are typically combined in the vapor phase, at temperatures in the range of 300° C. to 500° C., and at elevated pressures. Such a process is disclosed in U.S. Pat. No. 4,737,592, issued Apr. 12, 1988 to Abrams et al., which is incorporated by reference in its entirety.

The catalyst is used in its acid form. Acid forms of molecular sieves can be prepared by a variety of techniques. Preferably, the molecular sieve used to prepare dimethylamine will be in the hydrogen form, or have an alkali or alkaline earth metal, such as Na, K, Rb, or Cs, ion-exchanged into it.

The process involves reacting methanol, dimethylether or a mixture thereof and ammonia in amounts sufficient to provide a carbon/nitrogen (C/N) ratio from about 0.2 to about 1.5, preferably about 0.5 to about 1.2. The reaction is conducted at a temperature from about 250° C. to about 450° C., preferably about 300° C. to about 400° C. Reaction pressures can vary from about 7-7000 kPa (1-1000 psi), preferably about 70-3000 kPa (10-500 psi). A methanol and/or dimethylether space time of about 0.01-80 kPa (10-500 psi). A methanol and/or dimethylether space time of about 0.01-80 hours, preferably 0.10-1.5 hours, is typically used. This space time is calculated as the mass of catalyst divided by the mass flow rate of methanol/dimethylether introduced into the reactor.

EXAMPLES

Examples 1-14

Boron-containing CHA was synthesized by preparing the gel compositions, i.e., reaction mixtures, having the compositions, in terms of mole ratios, shown in the table below. The resulting gel was placed in a Parr bomb reactor and heated in an oven at the temperature indicated below while rotating at the speed indicated below. Products were analyzed by X-ray diffraction (XRD) and found to be boron-containing molecular sieves having the CHA structure. The source of silicon oxide was Cabosil M-5 fumed silica or HiSil 233 amorphous silica (0.208 wt % alumina). The source of boron oxide was boric acid and the source of aluminum oxide was Reheis F 2000 alumina.

| Ex. # | SiO$_2$/B$_2$O$_3$ | SiO$_2$/Al$_2$O$_3$ | H$_2$O/SiO$_2$ | OH−/SiO$_2$ | Na+/SiO$_2$ | SDA/SiO$_2$ | Rx Cond.[1] | Seeds | % 1-ada[2] |
|---|---|---|---|---|---|---|---|---|---|
| 1 | 2.51 | 1,010 | 23.51 | 0.25 | 0.20 | 0.25 | 140/43/5d | yes | 100 |
| 2 | 12.01 | 1,010 | 22.74 | 0.25 | 0.08 | 0.25 | 140/43/5d | yes | 100 |
| 3 | 12.33 | 1,010 | 22.51 | 0.25 | 0.08 | 0.25 | 140/43/5d | yes | 100 |
| 4 | 12.07 | 288,900 | 23.00 | 0.26 | 0.09 | 0.26 | 140/43/5d | no | 100 |
| 5 | 12.33 | 37,129 | 22.51 | 0.25 | 0.09 | 0.25 | 140/43/5d | yes | 100 |
| 6 | 12.33 | 248,388 | 22.51 | 0.25 | 0.09 | 0.25 | 140/43/5d | yes | 100 |
| 7 | 12.33 | 248,388 | 22.53 | 0.25 | 0.09 | 0.25 | 140/43/5d | yes | 100 |
| 8 | 12.33 | 248,388 | 22.53 | 0.25 | 0.00 | 0.25 | 140/43/5d | yes | 100 |
| 9 | 12.33 | 248,388 | 22.51 | 0.25 | 0.09 | 0.25 | 160/43/4d | yes | 100 |
| 10 | 11.99 | 288,900 | 23.18 | 0.26 | 0.09 | 0.26 | 160/43/4d | no | 100 |
| 11 | 12.13 | 288,900 | 32.22 | 0.43 | 0.21 | 0.21 | 160/43/4d | no | 100 |
| 12 | 11.99 | 288,900 | 23.16 | 0.26 | 0.00 | 0.26 | 160/43/4d | no | 100 |
| 13 | 11.99 | 288,900 | 23.18 | 0.26 | 0.09 | 0.26 | 160/43/4d | no | 100 |
| 14 | 3.08 | 248,388 | 22.51 | 0.25 | 0.00 | 0.25 | 160/43/6d | yes | 100 |

[1] ° C./RPM/Days
[2] 1-ada = Quaternary ammonium cation derived from 1-adamantamine The mole ratios of silicon oxide to boron oxide, and the Wt % yield on a silica basis, measured in some of the Examples of boron-containing CHA molecular sieves are shown below.

| Example # | SiO$_2$/B$_2$O$_3$ | Wt % Yield Based on Silica |
|---|---|---|
| 6 | 39 | 90.5 |
| 8 | 43 | 91.0 |
| 11 | 45 | 61.8 |
| 13 | 39 | 85.5 |

Examples 15-20

Deboronation

Boron was removed from samples of the molecular sieves prepared as described in Example 13 above and then calcined. The sample was heated in an acid solution under the conditions indicated in the table below. The results are shown in the table.

Comparative Examples 21-23

Aluminum and boron-containing CHA were synthesized according to the process of Example 1 in U.S. Patent Publication US2003/0176751. Comparative Example 21 used the same reaction mixture as in the patent publication, which was a mixture of ROH (R=N,N,N-trimethyladamantammoinium) solution, Al(NO$_3$)$_3$.9H$_2$O and tetraethylorthosilicate. Comparative Example 22 replaced an equimolar amount of the aluminum nitrate with boric acid. Comparative Example 23 replaced a double molar amount of the aluminum nitrate with boric acid.

The reactions were conducted in a plastic beaker until the weights of the formed gels were reduced. The gels were ground to a powder with mortar and pestle and placed into a Teflon lined autoclave. Then 1.6 g of 49% aqueous hydrofluoric acid was stirred in.

The mixtures were crystallized in an autoclave heated to 150° C. and tumbled at 43 rpm for 65 hours. X-ray diffraction analyses of the samples at 65 hours showed that all three comparative examples were clean highly crystalline chabazites. After cooling, the mixtures were washed to low conductivity (<80 micromho/cm) to remove extraneous aluminum or boron. Analysis of the products, and calculation of Wt % yield on a silica basis, gave the results as shown below:

| Example.# | Untreated (B)SSZ- 13 | Deboronation Rx | | | | | |
|---|---|---|---|---|---|---|---|
| | | 15 | 16 | 17 | 18 | 19 | 20 |
| Acid used | — | Acetic acid | acetic acid | acetic acid | HCl | HCl | HCl |
| Acid Molarity | — | 1.0 M | 0.01 M | 0.0001 M | 0.01 M | 0.001 M | 0.0001 M |
| Rx Cond. | — | 45 C./0 rpm/19 hr | 45 C./0 rpm/19 hr | 45 C./0 rpm/19 hr | 45 C./0 rpm/19 hr | 45 C./0 rpm/19 hr | 45 C./0 rpm/19 hr |
| | Untreated | Treated | Treated | Treated | Treated | Treated | Treated |
| Analysis Results Boron | 0.66% | 614 ppm | 513 ppm | 420 ppm | 421 ppm | 506 ppm | 552 ppm |

| Example No. | Si, wt % | Al, wt % | B, wt % | SiO2/ Al2O3 | SiO2/ B2O3 | Wt % Yield |
|---|---|---|---|---|---|---|
| 21 | 35.8 | 0.54 | <25 ppm | 128 | >11057 | 20.5 |
| 22 | 35.8 | 0.0103 | 0.0768 | 6703 | 360 | 20.7 |
| 23 | 33.8 | 0.0098 | 0.1740 | 6652 | 150 | 7.3 |

None of these comparative examples had a mole ratio of silicon oxide to boron oxide of between 15 and 125; even when a doubling of the molar concentration of boric acid was added to the reaction mixture. The reaction mixture with hydrofluoric acid used to produce the zeolite has a low Wt % yield of zeolite based on silica. The Wt % yields on a silica basis were all below 50 wt %.

What is claimed is:

1. A process for producing methylamine or dimethylamine comprising reacting methanol, dimethyl ether or a mixture thereof and ammonia in the gaseous phase in the presence of a catalyst comprising a boron-containing molecular sieve having the CHA crystal structure; and comprising (1) silicon oxide and (2) boron oxide or a combination of boron oxide and aluminum oxide, iron oxide, titanium oxide, gallium oxide and mixtures thereof; and wherein the mole ratio of silicon oxide to boron oxide in said boron-containing molecular sieve is between 15 and 125.

2. The process of claim 1 wherein the methanol, dimethylether or mixture thereof and ammonia are present in amounts sufficient to provide a carbon/nitrogen ratio from about 0.2 to about 1.5.

3. The process of claim 1 conducted at a temperature of from about 250° C. to about 450° C.

4. The process of claim 1 wherein oxide (2) is more than 50% boron oxide on a molar basis.

5. The process of claim 1, wherein the mole ratio of silicon oxide to boron oxide is between 15 and 100.

6. The process of claim 5, wherein the mole ratio of silicon oxide to boron oxide is between 15 and 50.

7. A method for producing methylamine or dimethylamine, comprising:
   a. selecting a catalyst comprising a boron-containing molecular sieve having a CHA crystal structure and a mole ratio of silicon oxide to boron oxide between 15 and 125;
   b. reacting methanol, dimethyl ether or a mixture thereof, and ammonia in the presence of the catalyst.

8. The method of claim 7, wherein the boron-containing molecular sieve is produced in a process with a Wt % yield based on silica of greater than 50.

9. The method of claim 7, wherein the boron-containing molecular sieve has a mole ratio of silicon oxide to boron oxide between 15 and 100.

10. The method of claim 9, wherein the boron-containing molecular sieve has a mole ratio of silicon oxide to boron oxide between 15 and 50.

11. The method of claim 8, wherein the boron-containing molecular sieve is produced in a process with a Wt % yield based on silica of greater than 60.

12. The method of claim 11, wherein the boron-containing molecular sieve is produced in a process with a Wt % yield based on silica of greater than 80.

13. The method of claim 12, wherein the boron-containing molecular sieve is produced in a process with a Wt % yield based on silica of greater than 90.

14. The method of claim 7, wherein the ammonia is in the gaseous phase.

* * * * *